United States Patent
Kataoka et al.

(10) Patent No.: US 6,927,033 B2
(45) Date of Patent: Aug. 9, 2005

(54) POLYMER COMPOSITION FOR FORMING SURFACE OF BIOSENSOR

(75) Inventors: Kazunori Kataoka, Tokyo (JP); Yukio Nagasaki, Moriya (JP); Hidenori Otsuka, Kawasaki (JP); Mitsuhiro Kaneko, Funabashi (JP)

(73) Assignee: Toudai TLO, Ltd., Tokyo (JP)

( * ) Notice: Subject to any disclaimer, the term of this patent is extended or adjusted under 35 U.S.C. 154(b) by 229 days.

(21) Appl. No.: 10/275,904

(22) PCT Filed: May 10, 2001

(86) PCT No.: PCT/JP01/03886

§ 371 (c)(1),
(2), (4) Date: Nov. 12, 2002

(87) PCT Pub. No.: WO01/86301

PCT Pub. Date: Nov. 15, 2001

(65) Prior Publication Data

US 2003/0171506 A1 Sep. 11, 2003

(30) Foreign Application Priority Data

May 11, 2000 (JP) ........................................ 2000-138472

(51) Int. Cl.$^7$ ............................................... G01N 33/53
(52) U.S. Cl. ...................... 435/7.1; 435/287.1; 435/817
(58) Field of Search ............................... 435/7.1, 287.1, 435/817, 283.1; 525/535; 528/370, 373, 374, 390

(56) References Cited

U.S. PATENT DOCUMENTS 5,204,239 A * 4/1993 Gitler et al. .................. 435/7.1

FOREIGN PATENT DOCUMENTS

| WO | 96/32434 | 10/1996 |
| WO | 96/33233 | 10/1996 |
| WO | 97/06202 | 2/1997 |

OTHER PUBLICATIONS

Ostuni, E. et al., *Colloids and Surfaces B: Biointerfaces*, vol. 15, pp. 3–30, (1999).

Paver, K.D., *Biomaterials*, vol. 20, No. 9, pp. 885–890, (1999).

* cited by examiner

*Primary Examiner*—Randy Gulakowski
*Assistant Examiner*—Christopher Keehan
(74) *Attorney, Agent, or Firm*—Wenderoth, Lind & Ponack, L.L.P.

(57) ABSTRACT

A polymer composition is provided, which contains a polymer or copolymer having a mercapto group at one end and functional group or ligand at the other end and also having a polyethylene glycol segment. Such a composition can form a biosensor surface of reduced non-specific adsorbability for proteins and the like.

5 Claims, No Drawings

POLYMER COMPOSITION FOR FORMING SURFACE OF BIOSENSOR

TECHNICAL FIELD

This invention relates to a polymer composition for forming surface of a biosensor utilizing surface plasmon resonance (SPR), biosensor chip surfaces onto which such a polymer is absorbed (or adsorbed), and a method for producing biosensor chips using the composition.

BACKGROUND ART

Surface plasmon resonance (SPR) is sensitive to changes in the index of refraction at and near the surface of a metal film (e.g., see A. Szabo, et al., *Curr. Opin. Strnct. Biol.* 5(1995)699–705). SPR enables an in situ observation of processes occurring between a surface and complex biological solutions that allows, e.g., the acquisition of data in real time without requiring tagging of the analytes. That is a technique convenient for obtaining both kinetic and thermodynamic parameters. Where biomolecules immobilized at a surface lead to changes in the index of refraction of the layer on which they are immobilized, SPR can also detect conformational changes of said biomolecules.

As a typical biosensor chip having this kind of surface, BIACORE which is commercially available from Amersham Pharmacia Biotech., Inc. can be named, which is provided in form of chips in which a matrix of dextran with carboxylated ends is immobilized on a translucent gold film. Such a dextran matrix exhibits a certain extent of resistance to non-specific adsorption of proteins, but because it has a considerable thickness (ca. 100 nm), in certain occasions it may have adverse influence on the thermodynamic and kinetic parameters where, for example, partitioning of the analyte in the matrix takes place.

On the other hand, E. Ostuni, et al., *Colloids and Surface B: Biointerfaces* 15(1999)3–30 discloses chips comprising a polymer represented by a general formula:

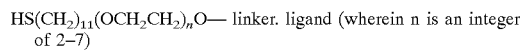
HS(CH$_2$)$_{11}$(OCH$_2$CH$_2$)$_n$O— linker. ligand (wherein n is an integer of 2–7)

as carried in the form of a self-assembled monolayer on a gold layer (12 nm) which is applied on a titanium thin layer (1–5 nm) vacuum-evaporated on a glass support. In said review, the authors suggest that the monolayer formed of said polymer having 2–7 ethylene glycol units exhibits resistance to adsorption of proteins. They further suggest that the above result would disagree with the theoretical prediction: for example, when polyethylene glycol (PEG) is grafted on a trichlorovinylsilane-modified glass, the shorter becomes the PEG chain, the more its resistance to adsorption of proteins would drop (S. I. Jeon, et al., *J. Colloid Interface Sci.* 142(1991)149–158).

However, polymers of small PEG units proposed by E. Ostuni, et al. in certain cases non-specifically adsorb specific proteins (e.g., those having positive electric charge as a whole), under the influence of metallic film surface.

DISCLOSURE OF THE INVENTION

The object of the present invention is to provide a polymer composition utilizing SPR, which can significantly reduce non-specific adsorption of any proteins irrelevantly to their kinds, and still can remove or significantly improve the defect inherent in the use of dextran matrix in BIACORE.

We have discovered that non-specific adsorption of biocomponents including proteins could be significantly reduced when a specific polymer having PEO segments which are regarded to be classified as a polymer, rather than an oligomer, is chemically absorbed (or adsorbed) onto a metal film, although so formed polymer matrix layer would be expected to have a far greater thickness than that of the matrix of said E. Ostuni, et al.

Accordingly, the present invention provides a polymer composition for forming surface of a biosensor utilizing surface plasmon resonance (SPR), which comprises the specific polymer (i.e., a polymer represented by the following general formula (I) as an active ingredient; and biosensor chips for detecting the SPR, which have adsorbed said polymer onto their surfaces:

general formula (I):

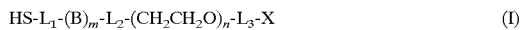
$$\text{HS-L}_1\text{-(B)}_m\text{-L}_2\text{-(CH}_2\text{CH}_2\text{O)}_n\text{-L}_3\text{-X} \qquad (I)$$

in which L$_1$, L$_2$ and L$_3$ each represents a valence bond or linker independently of each other, but where m is zero (0), L$_1$ and L$_2$ may together form a valence bond or a linker;

B stands for a formula,

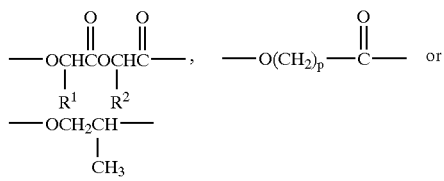

where R$^1$ and R$^2$ each independently stands for hydrogen atom or C$_{1-5}$ alkyl group and p is an integer of 2–5;

X stands for a hydrogen atom, functional group or ligand;

m is an integer of 0–10,000, and n is an integer of 10–20,000.

As another embodiment, the present invention provides a method for production of biosensor chips utilizing SPR, which is characterized by treating sensor chips having a metal surface selected from the group consisting of gold, silver, platinum and aluminum, with a solution or suspension of the polymer composition containing a polymer represented by above general formula (I), causing said surface to chemically adsorb or chemically absorb the polymer via the mercapto group in said polymer, and if necessary covalently bonding a ligand thereto via the functional group X in the polymer.

Also as still another embodiment, the present invention provides use of polymers represented by the general formula (I) for forming surfaces of biosensor chips utilizing SPR.

BEST MODE FOR CARRYING OUT THE INVENTION

Most of the polymers represented by the general formula (I) are known per se. Also those covered by the same formula which are deemed to be novel can be prepared in the manner similar to that for preparing the known polymers. Of these polymers, the preferred ones are those whose m in the general formula (I) ranges 0–10,000; $L_1$ stands for a valence bond or a linker of a formula,

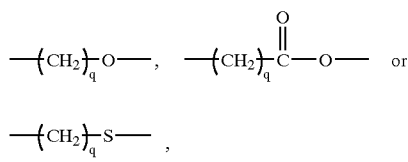

or where m is zero (0), $L_1$ and $L_2$ may together be a linker as defined above as to $L_1$, wherein q being an integer of 2–6; and where m is other than zero (0), $L_2$ is —O— or —O—CH$_2$CH$_2$—O—;

$L_3$ is a valence bond or —(CH$_2$)$_r$—, r being an integer of 1–6; and

X stands for a hydrogen atom, a functional group selected from the group consisting of aldehyde (—CHO), hydroxyl, amino, groups represented by the following formula

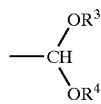

(in which $R^3$ and $R^4$ stand for either $C_{1-10}$ alkyl group independently of each other or are atomic groups together forming an optionally $C_{1-6}$ alkyl-substituted ethylene group), groups of the formula —NR$^5$R$^6$ (in which $R^5$ and $R^6$ stand for a hydrogen atom or a $C_{1-6}$ alkyl group independently of each other, provided either one of $R^5$ and $R^6$ is not hydrogen), acryloyl, methacryloyl, vinylbenzyl, allyl and p-toluenesulfonyl; or a ligand selected from the group consisting of sugar residue, biotin, antigen or antibody and nucleic acid.

Of these preferred polymers which are used in the present invention, those represented by the following general formula (I-a) can be named as examples of the polymers whose m is zero (0) referring to the general formula (I).

General formula (I-a):

HS—La—(CH$_2$CH$_2$O)$_n$—(CH$_2$)$_r$-Xa   (I-a)

in which La stands for

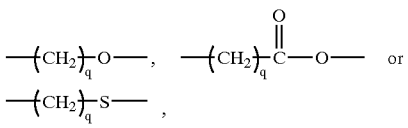

q being an integer of 2–6,
Xa is aldehyde group or

(where $R^3$ and $R^4$ either stand for $C_{1-10}$ alkyl independently of each other or are atomic groups together forming an optionally $C_{1-6}$ alkyl-substituted ethylene group),
n is an integer of 10–20,000, and
r is an integer of 1–6.

These polymers can be prepared by the methods disclosed in, for example, WO 96/32434, WO 96/33233, WO 97/06202, JP 11(1999)-322916 A and JP 11(1999)-322917 A, or if necessary modifying so prepared polymers or their precursors by methods known per se.

Although not in limitative sense, it is convenient to perform preparation of a polymer of the general formula (I) having a mercapto group at one end and a functional group or ligand at the other end, following the reaction schemes given hereafter, in which the individual steps can be practiced according to the methods known per se.

Scheme I (see: JP 11(1999)-322917 A):

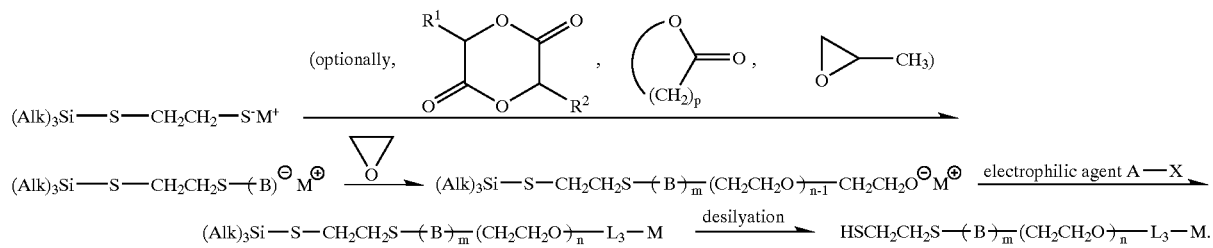

In the above formulae, Alk signifies $C_{1-6}$ alkyl; $M^+$ is a potassium ion; A is a leaving group such as halogen; $R^1$, $R^2$, X, n, m and $L_3$ have the above-defined significations; and B is

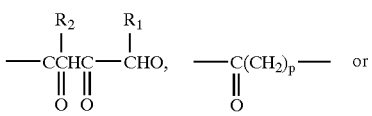

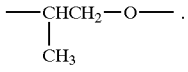

Scheme II (concerning preparation of the precursor polymers, see WO96/32434, WO96/33233 and WO97/06202):

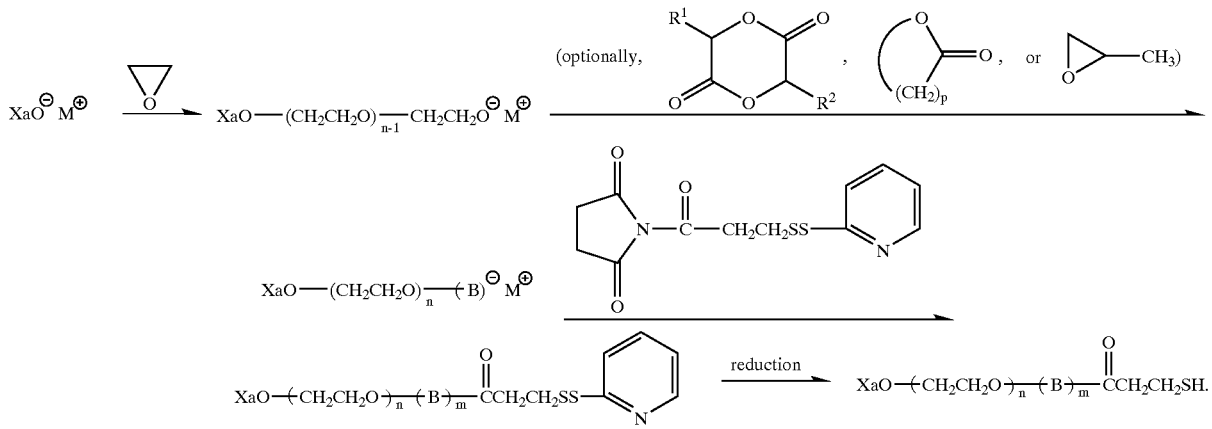

In the above formulae, Xa is X-L_3, and all other abbreviations and signs have the same significations as earlier given.

In the present specification, alkyl groups mean optionally branched alkyl groups, and $C_{1-6}$ or $C_{1-10}$ put before the words, "alkyl groups" mean that the number of carbon atoms in the alkyl groups are 1–6 or 1–10, respectively. Therefore, although not in limitative sense, as examples of such alkyl groups, methyl, ethyl, n-propyl, i-propyl, n-butyl, sec-butyl, tert-butyl, n-pentyl, n-hexyl, n-octyl, n-decyl and the like can be named.

A ligand as referred to in this invention can be the other member of a bonding pair capable of constituting a biological conjugate. For instance, biotin in biotin-avidin conjugate, sugar in sugar-lectin conjugate, antigen or antibody in antigen-antibody conjugate, and either of the nucleic acid in nucleic acid-nucleic acid hybrid may be named. These ligands can be introduced into one end of the polymer of the general formula (I), utilizing the reaction between the functional group (e.g., aldehyde group) present at said one end of the polymer and amino group in the ligand. It is also permissible to conduct such introduction of ligands after immobilizing a polymer having a functional group at one end on a metal surface as described later.

According to the invention, the number "n" of the polyethylene segment is at least 10, preferably 10–2500, inter alia, 50–500.

As above, the polymers of the general formula (I) each having a mercapto group at one end are stably soluble or dispersible in various solvents, for example, tetrahydrofuran, lower alkanol (e.g., ethanol), dimethylformamide, toluene, xylene, etc. Solutions or dispersions of polymers of the general formula (I) in these solvents constitute one embodiment of polymer compositions of the present invention for forming surfaces of biosensors utilizing SPR. Such a polymer composition may contain more than one kind of polymer, and where necessary, other additive(s), for example, an inorganic salt such as potassium sulfate may be incorporated, to enable immobilization of the polymer or polymers on the surface at a high density.

Thus formulated polymer compositions in general may take any form, which are contacted with chips formed of glass or silicon wafer on which a layer of gold, silver, platinum, palladium, aluminum or the like is deposited, where necessary via a titanium film which is vacuum-evaporated on the wafer to improve adhesivity of gold, silver, aluminum, etc., and whereby chemically absorbed (or adsorbed) onto the gold, silver or platinum. Chemical absorption (or adsorption) is not restricted by theories, but is understood to occur through formation of metal-thiolate (which may hereafter be referred to as conjugate) through reaction of mercapto groups of the polymers with the metal surface. This absorption (or adsorption) is conducted, for example, by immersing a support carrying a translucent gold film in aforesaid polymer solution or flowing the polymer solution over the support surface. While the optimum treating temperature varies depending on the kind of the polymer used, generally it can be within the range between melting point and boiling point of the solvent used. Considering operational ease, temperatures in the vicinity of room temperature are convenient. When treated at around the room temperature, normally sufficient contact time between the metal surface and polymer solution is around 30 minutes, while it may be prolonged to 1–24 hours or even more. The polymer or polymers of the general formula (I) are thus absorbed (or adsorbed) onto the metal surface. If required, unabsorbed (or unadsorbed) polymer may be washed away.

The polymer concentration in such a polymer solution is not critical so long as the polymer is completely dissolved or uniformly dispersed, while generally preferred range is 10–200 μg/ml.

The metal surface (e.g., surface of a sensor chip) onto which a polymer or polymers of the general formula (I) are chemically absorbed (or adsorbed) via the mercapto group(s) as provided through above procedures is covered with polyethylene glycol segment(s) of adequate chain length(s), and is substantially free of direct influences from the metal surface and the surface charge is expected to become zero or endlessly approach zero. Consequently, at the surface formed of the composition of the invention on the metal, non-specific adsorption of biomolecular species (e.g., positively charged protein) attributable to surface electric charge does not substantially take place, while such non-specific adsorption is occasionally observed at metal surfaces covered with alkylene thiol having a terminal composed of, for example, less than 10 ethylene glycol units.

The present invention is more specifically explained hereinafter, referring to concrete examples which, however, are not intended to limit the invention thereto. In the following, furthermore, polyethylene segment is abbreviated as PEG.

PRODUCTION EXAMPLE 1

Synthesis of a polymer having a mercapto group at one end and an acetal group-containing heterotelechelic PEG at the other end 1. Synthesis of acetal-PEG-SH (Mn=5000)

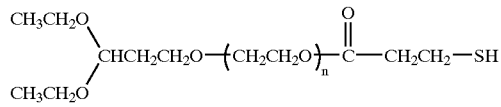

Distilled tetrahydrofuran (THF) 20 ml, and 3,3-diethoxy-1-propanol, an initiator, 0.2 mmol (0.032 ml) were added to an argon-substituted reactor, and further an equivalent amount of potassium naphthalene was added, followed by 15 minutes' stirring to conduct metallization. Then ethylene oxide 22.7 mmol (1.135 ml) was added, followed by two days' stirring to conduct polymerization. As a reaction-suspending agent, N-succinimizol-3-(2-piryridylthio) propionate (SPDP) 0.4 mmol (0.125 g) was dissolved in a small amount of distilled THF and into the resultant solution said polymerization reaction solution was dropped under cooling with ice, through an isopiestic dropping funnel. After an overnight stirring the reaction was suspended and the polymer was recovered by the series of operations as washing with saturated saline solution, extraction with chloroform, reprecipitation from ethylene and freeze drying from benzene. The construction of the recovered polymer was confirmed with $^1$H-NMR, and the amount of SPDP residue introduced to the polymer terminal was confirmed by UV absorption of 2-thiopyridone which was released upon reaction with 2-mercaptoethanol.

PEG-SS-Py $2.0 \times 10^{-2}$ mmol (100 mg) was dissolved in distilled water 4 ml, to which further 5 molar times thereof of dithiothreitol 0.1 mmol (15.42 mg) was added, followed by 30 minutes' stirring at room temperature. After the reaction, the polymer (hereafter abbreviated as PEG 5000) was recovered through a series of operations as washing with saturated saline water, extraction with chloroform and reprecipitation from ether. The construction of the recovered polymer was confirmed with $^1$H-NMR and the amount of terminal SH group was determined by the reaction with 2-pyridyldisulfide (2-PDS).

Furthermore, substantially the same operations as above were repeated except that the feed amount of ethylene oxide was decreased and increased in respective runs, to produce polymers of Mn=2,000 and Mn=10,000, respectively, which are hereafter abbreviated as PEG 2,000 and PEG 10,000. Mn represents the molecular weight of respective PEG segments.

EXAMPLE 1

Immobilization of PEG onto JI Sensor Chips

Each of the polymers obtained in above Production Example 1 was dissolved in a boron buffer of pH=8.0 and prepared solutions of 1,5,10,20 and 50 μg/ml as converted to SH-containing PEG (the concentration levels given herein are those regarding SH-containing PEG, which are approximately twice in terms of PEG concentration levels because the actual samples contain OH end groups). Flowing those solutions over JI sensor chip (BIACORE-originated) at a flow rate of 5 μl/min. for an hour, further 0.5% sodium dodecylsulfate (SDS) was flown at a rate of 10 μl/min. for 30 minutes to wash non-specific adsorbate away, and the substance bound onto the gold surfaces of the chips was quantified.

The results of the quantification are shown as RU saturation values, which were obtained as follows. RU values [a coefficient so set that 1 ng/mm$^2$ of the substance adsorbed onto said surface corresponds to 1000RU by, in said BIA-CORE biosensor system utilizing surface plasmon resonance, irradiating laser beam having a specific wavelength in such a manner to cause its total internal reflection and measuring the index of refraction) before adsorption of PEG 2000, PEG 5000 and PEG 10000, respectively (RU start) and after the adsorption and washing with SDS (RU$_{SDS}$)] were determined, and the values obtained by subtracting respective RU start values from RU$_{SDS}$ values were indicated as RU saturation values. Further, these RU saturation values were divided by the molecular weight of used polymer and the number of adsorbed polymer chains per 1 nm$^2$ was indicated as the immobilized polymer density.

The results are collectively shown in the following Table 1.

TABLE 1

Characteristics of Each of Treated Surfaces

| Polymer | Polymer Concentration Flown Over Surface (μg/ml) | RU Saturation Value | Immobilized Polymer Density (number of chains/nm$^2$) |
|---|---|---|---|
| PEG2000 | 100 | 1500 | 0.56 |
| PEG5000 | 50 | 1500 | 0.18 |
| PEG10000 | 100 | 2300 | 0.14 |

EXAMPLE 2

Adsorption Characteristics of Various Proteins onto Adsorptive Polymer Surfaces

Onto the surfaces of those JI sensor chips having the treated surfaces as prepared in Example 1 and onto those of CM5 (prepared by adsorbing dextran onto JI sensor chips: BIACORE-originated), each 1 mg/ml (10 mM of PBS, pH 7.4) solution of bovine serum albumin (BSA: molecular weight 69000; isoelectric point 4.9), lysozyme (Lysozyme: molecular weight 14300; isoelectric point 11) and avidin (Avidin: molecular weight 68000; isoelectric point 10–10.5) was flown at a rate of 5 μ/min. for 20 minutes, to draw an adsorption curve each. Thereafter the procedures as described in Example 1 was followed to provide each of RU values. The adsorption amounts (RU) of BSA, Lysozyme and Avidin were as shown in the following Tables 2,3 and 4, respectively.

TABLE 2

BSA Adsorption [RU] on Each Surface

| Polymer | Immediately after protein adsorption |
|---|---|
| PEG2000 | 1154.7 |
| PEG5000 | 499.6 |
| PEG10000 | 645.6 |
| CM5 | 123.5 |

TABLE 3

Lysozyme Adsorption [RU] on Each Surface

| Polymer | Immediately after protein adsorption |
|---|---|
| PEG2000 | 1358.0 |
| PEG5000 | 1038.0 |
| PEG10000 | 1413.4 |
| CM5 | 18775.0 |

TABLE 4

Avidin Adsorption [RU] on Each Surface

| Polymer | Immediately after protein adsorption |
|---|---|
| PEG2000 | 2364.2 |
| PEG5000 | 1710.4 |
| PEG10000 | 1784.4 |
| CM5 | 32694.9 |

Those results indicated in above tables show significantly reduced non-specific adsorption of various proteins onto PEG 2000, PEG 5000 and PEG 10000, from that onto CM5 with dextran-adsorbed surface. In particular, in respect of Lysozyme and Avidin, the adsorption values decreased to about 1/15–1/20.

Industrial Utilizability

According to the present invention, sensor chips in which non-specific adsorption of biocomponents onto the biosensor surfaces are eliminated are provided. They, therefore, can be used by biosensor producing industries and for diagnoses using such sensors.

What is claimed is:

1. Biosensor chips in which a polymer represented by the following general formula (I) is absorbed (or adsorbed) onto the sensor chip surfaces via the mercapto group present at one end of said polymer:

general formula (I)

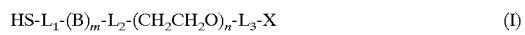

in which $L_1$, $L_2$ and $L_3$ represent valence bonds or linkers independently of each other, but where m is zero (0), $L_1$ and $L_2$ may together form a valence bond or a linker; B stands for a formula,

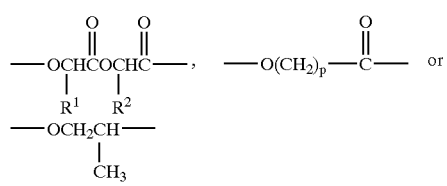

where $R^1$ and $R^2$ each independently stands for hydrogen atom or $C_{1-5}$ alkyl group and p is an integer of 2–5;

X stands for a hydrogen atom, functional group or ligand;

m is an integer of 0–10,000, and n is between an integer which provides a number average molecular weight of 2,000 and an integer of 20,000.

2. Biosensor chips according to claim 1, in which surfaces of the sensor chips are formed of at least one metal selected from the group consisting of gold, silver, platinum and aluminum.

3. A method for making biosensor chips which comprises contacting a solution or dispersion of a polymer represented by the following general formula (I):

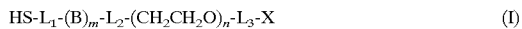

in which $L_1$, $L_2$ and $L_3$ represent valence bonds or linkers independently of each other, but where m is zero (0), $L_1$ and $L_2$ may together form a valence bond or a linker;

B stands for a formula,

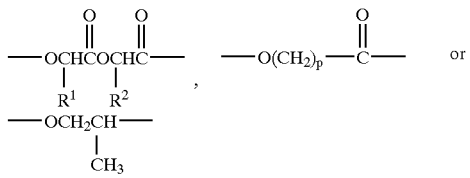

where $R^1$ and $R^2$ each independently stands for hydrogen atom or $C_{1-5}$ alkyl group and p is an integer of 2–5;

X stands for a hydrogen atom, functional group or ligand;

m is an integer of 0–10,000, and n is between an integer which provides a number average molecular weight of 2,000 and an integer of 20,000, with surfaces of sensor chips, said surfaces being formed of at least one metal selected from the group consisting of gold, silver, platinum and aluminum, whereby causing the polymer to be chemically adsorbed onto or chemically absorbed into said surfaces via the mercapto group present at one end of said polymer, and if necessary covalently bonding a ligand thereto via the functional group X.

4. Biosensor chips according to claim 1, in which, in formula (I), m is 0–10,000, n is an integer of 50–2500, $L_1$ stands for a valence bond or a linker of a formula:

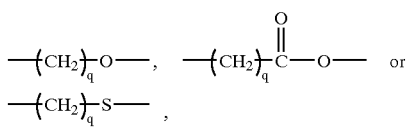

or, where m is zero (0), $L_1$ and $L_2$ may together be a linker as defined above as to $L_1$, wherein q is an integer of 2–6; and, where m is other than zero (0), $L_2$ is —O— or —O—$CH_2CH_2$—O;

$L_3$ is a valence bond or —$(CH_2)_r$—, r being an integer of 1–6; and

X stands for a hydrogen atom, a functional group selected from the group consisting of aldehyde (—CHO), hydroxyl, amino, groups represented by the following formula:

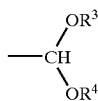

(in which $R^3$ and $R^4$ stand for either $C_{1-10}$ alkyl group independently of each other, or are atomic groups together forming an optionally $C_{1-6}$ alkyl-substituted ethylene group), groups of the formula $—NR^5R^6$ (in which $R^5$ and $R^6$ stand for a hydrogen atom or a $C_{1-6}$ alkyl group independently of each other, provided either one of $R^5$ and $R^6$ is not hydrogen), acryloyl, methacryloyl, vinylbenzyl, allyl and p-toluenesulfonyl; or a ligand selected from the group consisting of sugar residue, biotin, antigen or antibody and nucleic acid.

5. Biosensor chips according to claim 1, in which the polymers represented by the formula (I) are those expressed by the following general formula (I-a):

$$HS—La—(CH_2CH_2O)_n—(CH_2)_r-Xa \quad (I\text{-}a)$$

in which La stands for:

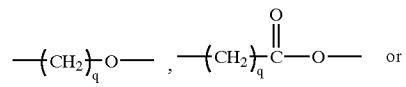

-continued

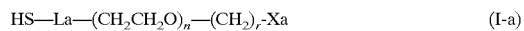

q being an integer of 2–6,
Xa is aldehyde group or

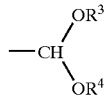

(where $R^3$ and $R^4$ either stand for $C_{1-10}$ alkyl independently of each other, or are atomic groups together forming an optionally $C_{1-6}$ alkyl-substituted ethylene group),
n is an integer of 50–2500, and
r is an integer of 1–6.

* * * * *